(12) United States Patent
Van Knippenberg et al.

(10) Patent No.: US 12,727,846 B2
(45) Date of Patent: Sep. 8, 2026

(54) BLOOD VELOCITY DETERMINATION

(71) Applicant: KONINKLIJKE PHILIPS N.V., Eindhoven (NL)

(72) Inventors: Luuk Anton Eli Maria Van Knippenberg, Eindhoven (NL); Johannes Antonius Van Rooij, Best (NL); Krishnamoorthy Palanisamy, Bangalore (IN); Sergei Y. Shulepov, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 630 days.

(21) Appl. No.: 18/039,513

(22) PCT Filed: Nov. 28, 2021

(86) PCT No.: PCT/EP2021/083263

§ 371 (c)(1),
(2) Date: May 31, 2023

(87) PCT Pub. No.: WO2022/117469

PCT Pub. Date: Jun. 9, 2022

(65) Prior Publication Data

US 2024/0000415 A1 Jan. 4, 2024

(30) Foreign Application Priority Data

Dec. 1, 2020 (EP) .................................... 20211086

(51) Int. Cl.

| | |
|---|---|
| ***A61B 8/06*** | (2006.01) |
| ***A61B 8/00*** | (2006.01) |
| ***A61B 8/08*** | (2006.01) |

(52) U.S. Cl.
CPC .............. *A61B 8/06* (2013.01); *A61B 8/0891* (2013.01); *A61B 8/488* (2013.01); *A61B 8/5246* (2013.01)

(58) Field of Classification Search
CPC ......... A61B 8/06; A61B 8/0891; A61B 8/488; A61B 8/5223
See application file for complete search history.

(56) References Cited

U.S. PATENT DOCUMENTS 4,476,874 A 10/1984 Taenzer
5,515,857 A 5/1996 Tsujino
(Continued)

FOREIGN PATENT DOCUMENTS

CN 105708494 A 6/2016
CN 106955098 A 7/2017
JP 09248304 A 9/1997

OTHER PUBLICATIONS

International Search Report Dated Feb. 21, 2022 For International Appln No. PCT/EP2021/083263 Filed Nov. 28, 2021.
(Continued)

*Primary Examiner* — Jason M Ip

(57) ABSTRACT

A method is provided for estimating blood velocity in vessel, for example for use in deriving a measure of blood flow through the vessel. The method comprises two stages. In a first stage, multiple measurements of blood velocity are acquired, using ultrasound data, at different radial positions across a blood vessel cross-section. A velocity profile is determined (velocity as a function of measurement location across the vessel cross-section) based on this. In a second stage, in one or more subsequent cardiac cycles, new ultrasound data is acquired and a blood velocity measurement acquired at a single location. The single blood velocity measurement preferably corresponds to a location of maximum velocity. This single measurement, in combination
(Continued)

with the personalized velocity profile already derived, is used to derive a measure of average blood velocity within the vessel.

20 Claims, 3 Drawing Sheets

(56) References Cited

U.S. PATENT DOCUMENTS

| | | | | |
|---|---|---|---|---|
| 6,477,406 | B1 * | 11/2002 | Turcott ................ | A61B 5/0002 607/36 |
| 2002/0013530 | A1 | 1/2002 | Cespedes | |
| 2002/0026547 | A1 | 2/2002 | Rodriguez | |
| 2007/0167794 | A1 * | 7/2007 | Dala-Krishna .......... | A61B 8/06 600/455 |
| 2009/0131765 | A1 * | 5/2009 | Roschak ................ | A61B 8/488 600/453 |
| 2023/0210490 | A1 * | 7/2023 | He .......................... | A61B 8/52 600/407 |

OTHER PUBLICATIONS

Torvid Kiserud, Leif Rune Hellevik and Mark Adrian Hanson, "Blood Velocity Profile in the Ductus Venousus Inlet Expressed by the Mean/Maximum Velocity Ratio", Ultrasound in Med. & Biol., vol. 23, No. 9, pp. 1301-1306, 1998.

Paul A. Picot and Paul M. Embree, "Quantitative vol. Flow Estimation Using Velcity Profiles", IEEE Trnasaction on Ultrasonics, Ferroelectrics and Frequency Control, vol. 41, No. 3, May 1994.

* cited by examiner 42
r
28
l r
v v
46
-1
-0.5
0
0.5
1
r 42
r
28
l 52
50
54
28

BLOOD VELOCITY DETERMINATION

CROSS-REFERENCE TO PRIOR APPLICATIONS

This application is the U.S. National Phase application under 35 U.S.C. § 371 of International Application No. PCT/EP2020/083263, filed on Nov. 28, 2021, which claims the benefit of European Application No. 20211086.2 filed on Dec. 1, 2020. These applications are hereby incorporated by reference herein.

FIELD OF THE INVENTION

The present invention relates to a method for determining a measure of blood velocity in a blood vessel, in particular using ultrasound data.

BACKGROUND OF THE INVENTION

Blood velocity can be used to derive a number of different hemodynamic parameters. One of these is blood flow. Since blood flow is related to cardiac output and also to tissue perfusion, it is a valuable parameter for assessing cardiovascular status.

Blood flow through a vessel depends upon blood velocity through the vessel and cross-sectional area of the vessel. The blood velocity however varies across the radial cross-section. To estimate blood velocity non-invasively, three main approaches can be distinguished. These are outlined below with reference to FIG. 1 which schematically illustrates blood velocity (y-axis) as a function of radial location (x-axis) within a blood vessel.

In a first approach, the blood vessel diameter is estimated from a B-mode image (assuming circularity) and a maximum blood velocity is measured in a radial center of the vessel using spectral Doppler ultrasound with a small Doppler gate size. The Doppler gate setting for the maximum velocity measurement is schematically illustrated in FIG. 1 with bar 12. The maximum velocity measurement is schematically illustrated with dotted line 14. A pre-determined radial velocity profile 18 (blood velocity as a function of radial measurement position in the vessel), is assumed to apply, for example parabolic for peripheral vasculature, or flat for locations such as the aortic arch where the flow is subject to large accelerations. The measured maximum velocity 14 is converted to an average velocity based on the assumed velocity profile. The volume flow rate may then be calculated as the product of the measured average velocity and the cross-sectional area of the vessel.

Since the velocity profile in vessels can in fact vary, this method lacks accuracy. However, this method is relatively fast, since only data from one small sample volume needs to be acquired and processed.

In a second approach, a larger spectral Doppler gate 22 can be used, that covers for example the whole, or a majority, of the diameter of the vessel. As a consequence, the acquired Doppler shift measurement within the sample volume represents the average flow velocity in the vessel. The example velocity measurement obtained in this approach is illustrated with dotted line 24.

However, the accuracy of this method strongly depends on the uniformity of the ultrasound intensity and the distribution of scatterers within the sample volume. If the uniform insonification condition is met, the power spectral density of the Doppler signal represents the distribution of red cell velocities within the sample volume and the spatial mean velocity may be calculated from the intensity-weighted, mean Doppler shift. However, if this condition is not met, the results can lack accuracy.

A third approach is based on acquiring multiple blood velocity measurements across a range of different radial positions. For example multiple spectral Doppler gates covering different locations, or color Doppler, can be used to determine the velocity profile in the vessel. FIG. 1 schematically illustrates a plurality of individual velocity measurements with the series of circles 28. These show the velocity measurement value (y-axis) as a function of radial location (x-axis) of the measurement within the vessel. The Doppler ultrasound measurement gates corresponding to the plurality of velocity measurements is shown with line 30. An average flow velocity can be calculated using the plurality of velocity measurements 28 by integrating the acquired velocity profile with respect to the vessel radius. This method requires small sample volumes (i.e. localized measurement positions) to be accurate. However, since multiple measurements need to be made, greater computational power is required and, depending on the implementation, more ultrasound transmit events are required. Thus, this method is slower, and more resource intensive.

A new approach to measuring blood velocity would be of value.

SUMMARY OF THE INVENTION

The invention is defined by the claims.

According to examples in accordance with an aspect of the invention, there is provided a method for determining a measure of blood velocity in a blood vessel of a subject, the method comprising:

(a) in a first cardiac cycle:
- acquiring ultrasound data of the blood vessel,
- determining a blood velocity profile across a radial cross-section of the blood vessel during the cardiac cycle using the ultrasound data, based on acquiring a plurality of blood velocity measurements at different radial positions across the vessel radial cross-section; and (b) in one or more subsequent cardiac cycles:
- acquiring ultrasound data of the blood vessel,
- measuring a blood velocity at a single point within the radial cross-section of the vessel using the ultrasound data, and
- calculating an average blood velocity across the radial cross-section of the vessel based on the measured velocity at the single point and the velocity profile.

Preferably, the method is performed in a single measurement or examination session, i.e. (a) and (b) are performed in the same measurement or examination session.

As discussed above, various known approaches exist for determining blood velocity. One of these is to acquire multiple measurements of blood velocity at different radial positions of the vessel, and then determine flow based on an 'average' velocity determined by integrating across the whole set of velocity measurements. This approach is the most accurate. A second, faster, approach is to take only a single velocity measure at one radial position, and then estimate an 'average' velocity across the whole cross section based on a pre-defined conversion or transfer function. This is less accurate but faster.

Embodiments of the present invention are based on optimizing the advantages of both approaches. In particular, the method comprises a first and second phase. In a first phase, (a), a velocity profile is determined for the specific patient based on acquiring multiple velocity measurements across the radial cross-section of the vessel. Then, in a second phase, (b), of the same examination session, an 'average' velocity is computed for subsequent heart cycles based on acquiring just a single velocity measurement, and using the computed subject-specific velocity profile to convert this accurately to an average velocity. This can then be used to determine a blood flow.

Embodiments of the invention thus achieve the accuracy benefits of the velocity integration approach, due to explicit calculation of the velocity profile for the patient, while still achieving the speed benefits of the estimated velocity approach by re-using the same single velocity profile determined earlier in the method. The method effectively front-loads the processing and time demands of the velocity profile estimation, meaning that subsequent velocity calculations can be done much more quickly.

Determining the velocity profile comprises acquiring a set of measurements of the blood velocity at different radial positions spanning the diameter or radius of the vessel (spanning the radial cross-section of the vessel).

In other words, the velocity profile effectively comprises a representation of blood flow velocity as a function of radial position across a radial cross-section of the blood vessel.

A record of the derived velocity profile may be stored in a local or remote datastore. As an alternative to storing a record of the whole velocity profile, a ratio or conversion factor can be computed, which is the ratio of the single velocity measurement (e.g. a maximum velocity value), to an average velocity (as computed from the plurality of measurements used to derive the profile). This ratio or conversion factor may then be stored and used in phase (b) for converting subsequently acquired values of the single velocity measurement to values of average velocity.

The radial cross-section means a section orthogonal to the longitudinal axis of the vessel.

In accordance with one or more embodiments, measuring the blood velocity at the single point of the vessel may be performed using spectral Doppler ultrasound data. This may be pulse wave Doppler ultrasound data.

The velocity profile is measured contemporaneously with the determination of the average blood velocity. Preferably (a) and (b) are performed in the same measurement session. In some examples, the ultrasound data acquired in (a) and (b) is acquired from the same measurement position.

The same measurement session may mean that phase (b) is performed directly subsequent to performing phase (a). Phase (b) may be performed using the same ultrasound transducer unit (e.g. probe) as phase (a). Phase (b) may be performed with the ultrasound transducer unit in the same position relative to the body as phase (a). Phase (b) may be performed subsequent to phase (a) and with the ultrasound transducer unit unmoved compared to phase (a).

In some examples, the ultrasound data acquired in (a) and (b) is acquired using the same ultrasound transducer unit. The ultrasound transducer unit may be held stationary between (a) and (b).

In preferred examples, the acquired blood velocity measurement at the single point of the vessel represents a maximum velocity of the blood flow. Using the velocity profile, an accurate estimation of an average blood velocity across the vessel diameter can be determined. As explained further below, this may be a point at a radial center of the vessel, or may be located offset from the center, depending upon the vessel geometry.

There are different ways of determining a point of maximum velocity. A procedure can be executed for identifying a location of maximum velocity. This may comprise an iterative gate-adjustment procedure wherein an initial gate location is chosen and is adjusted based on determining a quality factor indicative of how well the set gate size and position compare to the location of the maximum velocity in the estimated velocity profile.

In accordance with one or more embodiments, the determining of the velocity profile may further comprise acquiring blood velocity measurements at different circumferential positions for each of the different radial positions. This thus provides a 2D velocity profile comprising blood velocity measurement at different radial and circumferential positions.

In accordance with one or more embodiments, phase (a) may be executed once, and (b) repeated recurrently for multiple cardiac cycles following execution of (a), using the same velocity profile obtained in (a). Thus, the same velocity profile is re-used for multiple measurement instances, conserving processing resource, and improving efficiency.

In accordance with one or more embodiments, the method may further comprise obtaining an indication of at least one hemodynamic parameter of the subject and triggering re-execution of (a) responsive to detection of the at least one hemodynamic parameter meeting one or more pre-defined criteria. The one or more pre-defined criteria may for example include a threshold value for the at least one hemodynamic parameter. The criteria may include the at least one hemodynamic parameter exceeding a threshold or falling below a threshold.

An assessment procedure may be recurrently executed throughout the method, the assessment procedure comprising obtaining the measure of the at least one hemodynamic parameter and determining whether the one or more pre-defined criteria are met. The criteria may be retrieved from a local or remote datastore.

It is envisaged that phase (b) may be re-executed recurrently after execution of (a)—i.e. acquiring multiple recurrent measurements of the average velocity, and optionally also blood flow (based on the average velocity).

The at least one hemodynamic parameter may be monitored over the course of the multiple executions of (b), and the pre-defined criteria checked recurrently.

The at least one hemodynamic parameter may include, by way of non-limiting example, one or more of: heart rate, blood pressure, vessel diameter, volume flow, peak velocity, and arterial compliance.

In accordance with one or more embodiments, the at least one hemodynamic parameter may be obtained based on processing of the ultrasound data of the blood vessel acquired in (b). Thus this avoids the need to perform a further acquisition event, or to use data from a further source, in order to determine the hemodynamic parameter. This hence increases efficiency.

In accordance with one group of embodiments, the phase point within the cardiac cycle at which the velocity profile is acquired is taken into account in the calculations.

In some examples, the velocity profile may be measured recurrently over the course of the first cardiac cycle, at different phase points of the cardiac cycle, to acquire a respective velocity profile for each of the different phase points of the cardiac cycle.

Phase (b) of the method may then comprise determining a phase point of the cardiac cycle at which the velocity at the single point was determined and wherein the calculating of the average velocity is performed based on the velocity profile as measured in (a) at a corresponding phase point of the cardiac cycle.

The measurement of the blood velocity has a number of useful applications. It can be used in the determination of a range of different hemodynamic parameters for example. In accordance with one set of embodiments, the blood velocity measurement can be used to determine blood flow. Phase (b) of the method may comprise a further step of determining a blood flow through the blood vessel based on the determined average blood velocity. Phase (b) may further comprise a step of determining an area of the radial cross-section of the blood vessel using B-mode ultrasound data, and wherein the determining of the blood flow is based on the average blood velocity and the radial cross-section.

Examples in accordance with a further aspect of the invention provide a computer program product comprising code means configured, when run on a processor, to cause the processor to perform a method in accordance with any example or embodiment outlined above or described below, or in accordance with any claim of this application.

Examples in accordance with a further aspect of the invention provide a processing arrangement for use in determining a measure of blood velocity in a blood vessel during a single measurement session, the processing arrangement adapted to:

(a) in a first cardiac cycle:
- receive ultrasound data of the blood vessel,
- determine a blood velocity profile across a radial cross section of the blood vessel during the cardiac cycle using the ultrasound data, based on acquiring a plurality of blood velocity measurements at different radial positions across the vessel radial cross-section, and (b) in one or more subsequent cardiac cycles:
- receive ultrasound data of the blood vessel,
- measure a blood velocity at a single point within the radial cross-section of the vessel using the ultrasound data, and
- calculate an average blood velocity across the radial cross-section of the vessel based on the measured velocity at the single point and the velocity profile.

The processing arrangement may be further adapted to obtain an indication of at least one hemodynamic parameter of the subject and trigger re-execution of (a) responsive to detection of the at least one hemodynamic parameter meeting one or more pre-defined criteria.

In accordance with one or more embodiments, the at least one hemodynamic parameter may be obtained based on processing of the ultrasound data of the blood vessel acquired in (b).

In accordance with one or more embodiments, in (a), the velocity profile may be measured recurrently over the course of the first cardiac cycle, at different phase points of the cardiac cycle, to acquire a respective velocity profile for each of the different phase points of the cardiac cycle.

Phase (b) may comprise determining a phase point of the cardiac cycle at which the velocity at the central point was determined and the calculating of the average velocity is performed based on the velocity profile as measured in (a) at a corresponding phase point of the cardiac cycle.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
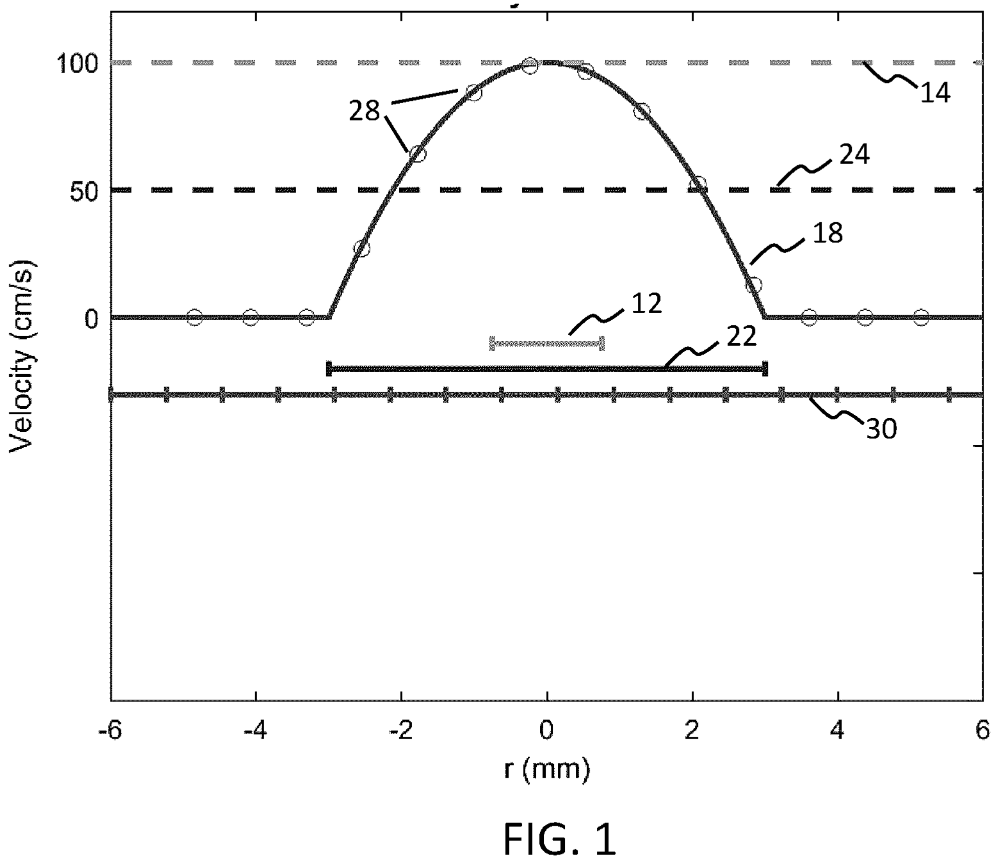
FIG. 1 schematically illustrates a set of known approaches to estimating blood velocity.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a method for estimating blood velocity in vessel, which optionally may be used to derive a measure of blood flow through the vessel. The method comprises two stages. In a first stage, multiple measurements of blood velocity are acquired, using ultrasound data, at different positions. A velocity profile is determined (velocity as a function of measurement location across a vessel cross-section) based on this. In a second stage, in one or more subsequent cardiac cycles, new ultrasound data is acquired and a blood velocity measurement acquired a single location (or a select one or more locations, fewer than were used for deriving the velocity profile). The single blood velocity measurement preferably corresponds to a location of maximum velocity. This single measurement, in combination with the personalized velocity profile already acquired for the subject, is used to derive a measure of average velocity.

Embodiments of the invention aim to combine the speed of the 'assumed-velocity-profile' method discussed above and the accuracy of the multi-gate approach (multiple velocity measurements) described above by measuring the velocity profile once and then using a conversion factor from the single velocity value (preferably maximum velocity) to the average velocity to estimate flow. As explained above, this conversion factor depends upon the velocity profile. Since the velocity profile in most vessels is somewhere between parabolic (conversion factor 0.5) and flat (conversion factor 1), an incorrect assumption regarding the profile can lead to a large error in the velocity calculation. By measuring a personalized velocity profile for the specific subject, embodiments of the present invention improve accuracy. However, by subsequently re-using this for multiple subsequent velocity measurements (in repeated iterations of phase (b) discussed above), this avoids unnecessary repetition of work, improving efficiency and frame rate. To further improve accuracy, the velocity profile may be re-measured responsive to detecting a threshold change in one or more particular hemodynamic parameters, indicative of a possible change in the blood velocity or flow rate.

Figure 2:
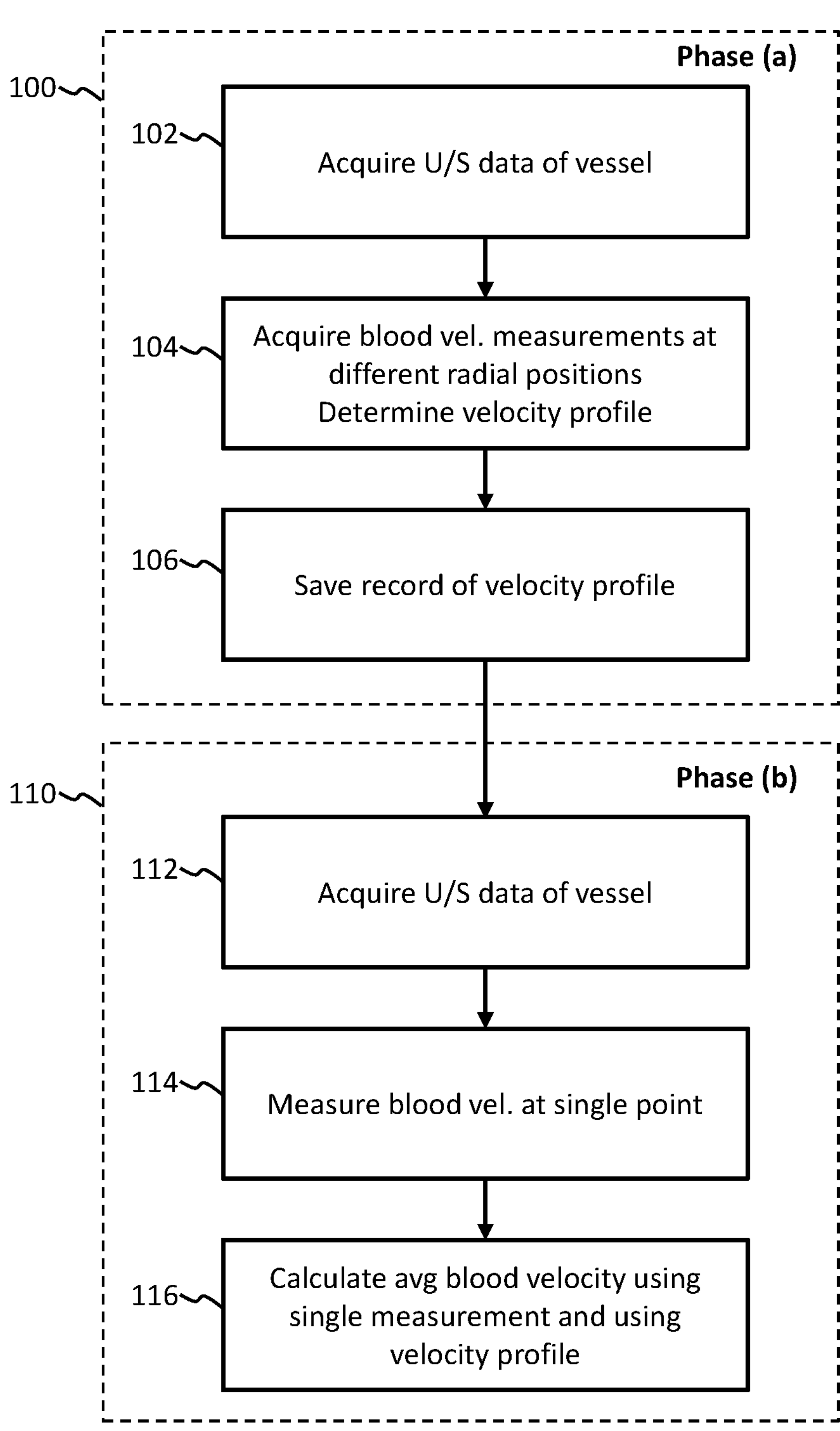
FIG. 2 outlines steps of an example method in accordance with one or more embodiments.

FIG. 2 outlines steps of an example method for obtaining a measure of blood velocity in accordance with one or more embodiments. The method will be summarized in brief first, before presenting more detailed discussion of the different steps. The method comprises: a first stage or phase 100, and a second stage or phase 110. The second phase may be repeated multiple times after a single execution of the first. The two phases are performed in the same single measurement session. For example phase (b) 110 may be performed directly subsequent to performing phase (a) 100. Phase (b) may be performed using the same ultrasound transducer unit (e.g. probe) as phase (a). Phase (b) may be performed with the ultrasound transducer unit in the same position relative to the body as phase (a).

Phase (a) 100 comprises, in a first cardiac cycle of the subject: acquiring 102 ultrasound data of the blood vessel. Phase (a) further comprises determining 104 a blood velocity profile across a radial cross-section of the blood vessel during the cardiac cycle using the ultrasound data, based on acquiring a plurality of blood velocity measurements at different radial positions across the vessel radial cross-section. Phase (a) may optionally further comprise saving a record of the velocity profile. Alternatively, a record may be saved of a computed ratio or conversion factor between a velocity value from a particular single location in the vessel (e.g. a maximum velocity location) to an average of the velocity values.

Phase (b) of the method comprises, in one or more subsequent cardiac cycles: acquiring 112 ultrasound data of the blood vessel; obtaining 114 a measure of blood velocity at a single location or region within the radial cross-section of the vessel using the ultrasound data; and calculating 116 an average blood velocity across the radial cross-section of the vessel based on the measured velocity at the single point and the velocity profile (or the computed ratio or conversion factor).

In advantageous embodiments, phase (a) may be executed once, and phase (b) repeated recurrently for multiple cardiac cycles following execution of (a), using the same velocity profile obtained in (a).

Figures 3, 4, 5, 6, 7:
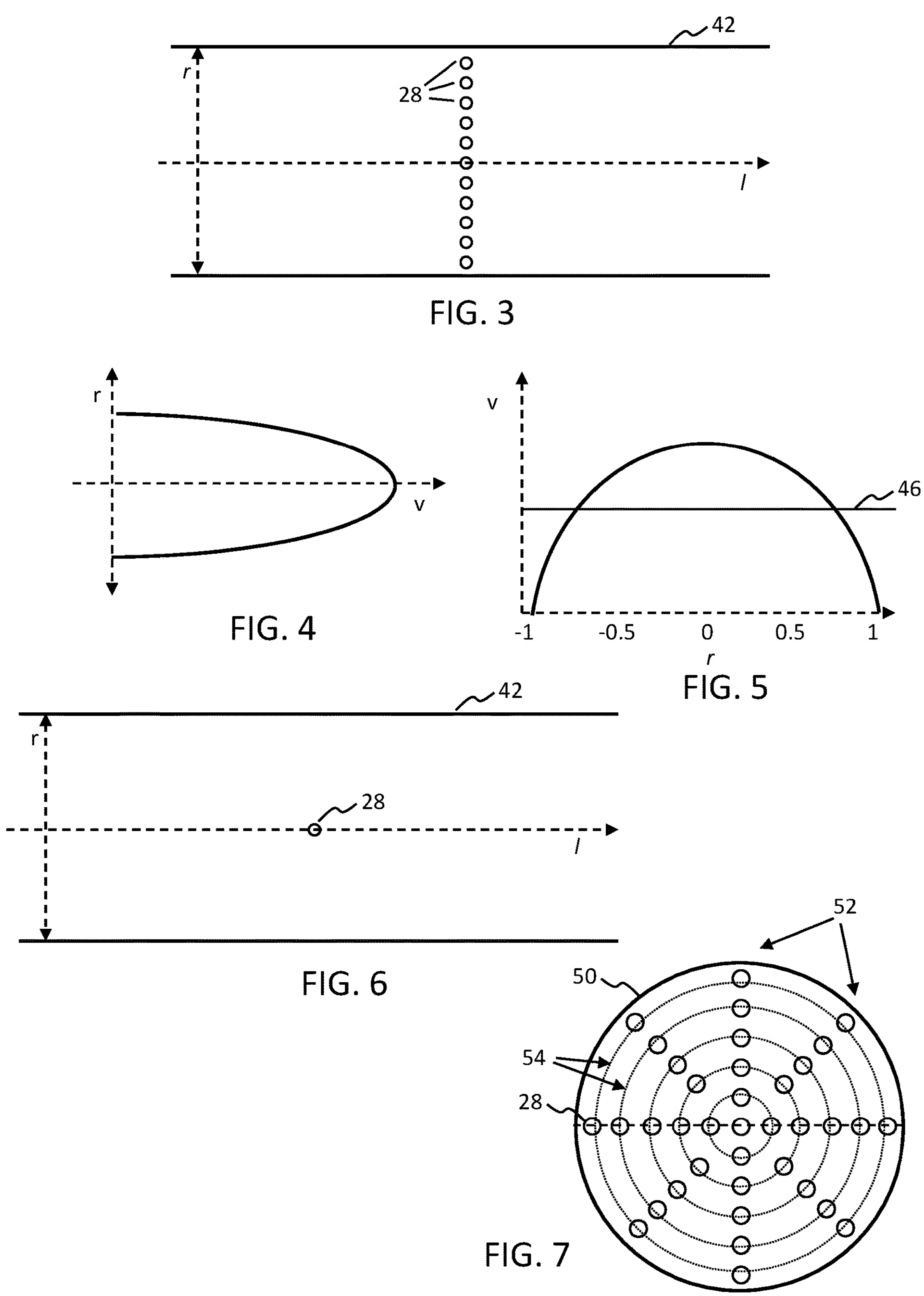
FIG. 3 illustrates acquisition of velocity measurements at multiple radial points for use in determining a velocity profile.
FIGS. 4 and 5 illustrate example velocity profiles.
FIG. 6 illustrates acquisition of a velocity measurement at a single radial location.
FIG. 7 illustrates acquisition of velocity measurements for determining a 2D velocity profile.

With regards to phase (a), FIG. 3 schematically illustrates acquisition of the plurality of blood velocity measurements 28 at different radial positions across a radial cross-section of a blood vessel 42. FIG. 3 depicts the blood vessel 42 across a longitudinal cross-section parallel a longitudinal, l, dimension of the vessel. The radial plane, defining a radial cross-section, is orthogonal the plane shown in FIG. 3.

Acquiring the plurality of velocity measurements 28 may be done for example using spectral Doppler ultrasound (e.g. pulse wave Doppler), or using color Doppler imaging. If spectral Doppler (e.g. pulse wave Doppler) is used, the plurality of velocity measurements are acquired using a corresponding plurality of small-width (spatial) gates. The gating can be applied post-acquisition to data captured in a single ultrasound data acquisition sequence (i.e. with post-processing of acquired spectral Doppler ultrasound data), or can be applied through performing multiple gated acquisitions. The latter approach may achieve greater accuracy since the ultrasound beam can be optimally focused for each gate. However, this increases scan time. Thus, instead, the data can be acquired in single acquisition event, but configured such that the acquired data includes data suitable for each of the different gates, i.e. the data for the different gates is acquired simultaneously. To do so, a single acquisition can be performed where the ultrasound beam is focused adequately along the full vessel width. In this case, gates are applied post-acquisition.

The required gate for each respective velocity measurement (at a respective location across the vessel cross-section) may be determined in advance or may be dynamically configured.

For color Doppler imaging, the measurement for each location may be obtained based on the velocity value across a small spatial image region containing the location. For example, the cross-section might be divided into a plurality of equally sized radial slices, and wherein a respective velocity measurement is obtained based on the mean color Doppler data for each.

Using the plurality of velocity measurements, a velocity profile across the radial cross-section can be determined. A velocity profile means a profile of the blood velocity as a function of position within the radial cross-section.

One example velocity profile is schematically illustrated in FIG. 4, which shows velocity on the x-axis and radial position on the y-axis. A further example is illustrated in FIG. 5, which shows velocity on the y-axis, radial position on the x-axis, and indicates a computed average 46 of the velocity measurements.

The velocity profile preferably represents at least blood velocity as a function of radial position. Optionally, the velocity profile may represent velocity as a function of both radial and circumferential position. In this case, a plurality of velocity measurements may be acquired at multiple circumferential positions for each of the different radial positions.

In advantageous embodiments, based on the acquired velocity profile, a maximum velocity measurement among the plurality of velocity measurements is identified, and an average (e.g. mean) of the plurality of velocity measurements is computed. A ratio may then be calculated of the maximum velocity to the mean velocity. This ratio may then be stored as a conversion factor for later use in converting a measured maximum velocity to an average velocity measurement.

Since the velocity profile may change during the course of a single cardiac cycle, the velocity profile (and optionally the conversion factor) may be measured at multiple time points within the cardiac cycle over which phase (a) is performed. As a result, the velocity profile measurement typically lasts for one cardiac cycle (e.g. around 1 second). An average of the velocity profiles at the multiple cardiac cycle phase points may be derived and used as the velocity profile for the stage (b) procedure. Alternatively, as will be explained below, a phase-dependent velocity profile may be used in stage (b) of the method.

With regards to phase (b) of the method, FIG. 6 schematically illustrates acquisition of a blood velocity measurement 28 at a single point within the radial cross-section of the vessel using the acquired ultrasound data. This may be acquired with spectral Doppler ultrasound acquisition. This measured velocity at a single point may be converted to an average blood velocity based on the previously obtained velocity profile. For example, if the single velocity measurement is obtained at location x within the radial cross-section, the velocity profile may be consulted to identify a ratio between the velocity value at location x in the profile, and an average velocity across all values in the profile. This ratio may then be applied to the single acquired value to convert it to an average velocity value for the vessel.

As discussed above, in preferred examples, the blood velocity measurement acquired at the single location or region in phase (b) is preferably a location or region coinciding with a location of maximum blood velocity in the vessel. A ratio of the maximum velocity measurement in the velocity profile to the average velocity of the velocity profile may be calculated in advance and used to obtain the average velocity measure in phase (b) of the method.

In accordance with one or more embodiments, the location of the maximum blood velocity point within the vessel cross-section may be assumed to be a region or location at a radial center of the blood vessel.

However, this assumption is not always accurate, e.g. due to curvature in the vessel. Thus, in accordance with one or more embodiments, the method may include a further step of determining a location within the blood vessel radial cross-section (a cross-section orthogonal to a longitudinal axis of the vessel lumen) at which a maximum blood velocity occurs. This may be determined from the plurality of blood velocity measurements acquired in phase (a) or from the velocity profile derived from these measurements. A record of the location of the maximum blood velocity, as measured in phase (a) may be stored. In phase (b), for acquiring the single blood velocity measurement, the Doppler gate position and size can be set based on the recorded location of the maximum blood velocity in phase (a).

However, a further complication is that a location of the maximum can in some cases vary throughout a single cardiac cycle. For example, in the systolic phase it is likely to be further from the vessel center, and during the diastolic phase it is likely to be closer to the center of the vessel. Thus, simply repositioning the Doppler gate based on a single maximum velocity location determined in phase (a) may in some cases not provide maximum accuracy. Thus, in accordance with one or more embodiments, a Doppler gate size may be chosen which is sufficiently wide to accommodate the small variations in the maximum velocity location over the cardiac cycle (i.e. it covers a range of possible positions). In some examples, the variation in the maximum velocity position over the course of a cardiac cycle could be measured or tracked in phase (a), or in a dedicated calibration phase preceding phase (a), and wherein the gate width and position is chosen so that it covers the full range of the maximum velocity positions, and for example with the median position over the cardiac cycle aligned with a center of the gate width.

Subsequent to deriving the average velocity in phase (b), the method may further comprise determining a measure of blood flow through the blood vessel based on the average velocity measure. For example, phase (b) may further comprise determining an area of the radial cross-section of the blood vessel, and wherein the determining of the blood flow is based on a product of the average blood velocity and the radial cross-section. The cross-sectional area may be derived using B-mode ultrasound imaging of the vessel. From a B-mode image of the vessel, a diameter of the vessel may be determined, and a cross-sectional area estimated (for instance by assuming circularity). Image analysis algorithms may be applied to determine the area more accurately, for instance model-based segmentation or edge-detection techniques may be used.

B-mode ultrasound acquisitions may be temporally interleaved with spectral Doppler acquisitions in repeated executions of phase (b). In other words, each iteration of phase (b) may comprise successively acquiring spectral Doppler data and B-mode imaging data.

As mentioned above, the velocity profile may be measured recurrently over the course of the first cardiac cycle (in phase (a)), at different phase points of the cardiac cycle, to acquire a respective velocity profile for each of the different phase points of the cardiac cycle.

Each iteration of stage (b) may then comprise determining a phase point of the cardiac cycle at which the velocity at the single point was determined and then calculating the average velocity based on the velocity profile as measured in stage (a) at a corresponding phase point of the cardiac cycle.

In relation to this set of embodiments, the frame rate of ultrasound data acquired in phases (a) and (b) may differ and thus it may be the case that there is not always an exact one-to-one match between the cardiac phase point at which data is acquired in an iteration of (b) and one of the multiple phase points for which a velocity profile was derived in phase (a). In this case, an interpolation may be performed between the velocity profiles of for the two most closely matching cardiac phase points (i.e. the closest phase points either side of the phase point in question).

It may in general be assumed that the velocity profile acquired in phase (a)—and the conversion factor from maximum to average velocity—remains accurate until a significant change in hemodynamics occurs. A change in hemodynamics can be observed in any of a range of different hemodynamic parameters such as, by way of non-limiting example: heart rate; blood pressure; blood vessel diameter; average vessel diameter over the cardiac cycle; vessel diameter in systole or diastole; volume flow; peak velocity; and arterial compliance.

Thus, in accordance with one or more embodiments, the method may further comprise obtaining an indication of at least one hemodynamic parameter of the subject and triggering re-execution of phase (a) responsive to detection of the at least one hemodynamic parameter meeting one or more pre-defined criteria.

The one or more pre-defined criteria may include a threshold value for the at least one hemodynamic parameter. The criteria may include the at least one hemodynamic parameter exceeding a threshold or falling below a threshold.

An assessment procedure may be recurrently executed throughout the method, the assessment procedure comprising obtaining the measure of the at least one hemodynamic parameter and determining whether the one or more predefined criteria are met. The criteria may be retrieved from a local or remote datastore.

It is envisaged that phase (b) may be re-executed recurrently after execution of (a)—i.e. acquiring multiple recurrent measurements of the average velocity, and optionally also blood flow (based on the average velocity).

The at least one hemodynamic parameter may be monitored over the course of the multiple executions of (b), and the pre-defined criteria checked recurrently.

It is noted that all of the mentioned hemodynamic parameters apart from blood pressure and arterial compliance can be directly derived from the obtained ultrasound measurement data. Thus, the at least one hemodynamic parameter may be obtained based on processing of the ultrasound data of the blood vessel acquired in phase (b).

As an alternative approach, the velocity profile may simply be re-acquired at fixed time intervals (e.g. every 30 seconds, depending on the application).

As mentioned above, in phase (a), determining of the velocity profile may further comprise acquiring blood velocity measurements at different circumferential positions for each of the different radial positions. This thereby provides a 2D velocity profile comprising blood velocity measurement at different radial and circumferential positons across a radial cross-section of the vessel.

This is schematically illustrated in FIG. 7 which shows a plurality of velocity measurements 28, which include measurements at multiple circumferential locations 52 within each of a plurality of radial positions or bands 54 across the radial cross-section 50. From this, a 2D velocity profile can be derived, indicative of blood velocity as a function of radial and circumferential position within the radial cross-section.

Embodiments of the invention may have particular utility for ultrasound monitoring applications, where the blood velocity, and optionally blood flow, are monitored over an extended period. In such circumstances, movement of the subject can disturb the measurements, since it shifts the spatial position of the spectral Doppler (Pulse Wave Doppler) ultrasound gate relative to the blood vessel. Re-adjustment of the gate position would therefore be required to restore full accuracy of the measurements.

In accordance with one or more embodiments, the method may further comprise detecting movement disturbances of the patient and adjusting the position of the ultrasound acquisition gate responsive to this. The method may comprise triggering re-adjustment of the gate position and size responsive to a detected movement exceeding a pre-determined threshold.

Movement of the patient may be detected for example using an auxiliary movement sensor (e.g. an accelerometer) coupled to the patient, e.g. to the patient's chest. Movement may additionally or alternatively be detected based on the acquired ultrasound data in phase (b). In particular, patient movement will typically result in a sudden change in (peak systolic) velocity, or in a loss of signal (i.e. if the Doppler gate is no longer within the vessel). Thus, patient movement can be detected based on detecting a threshold change in the velocity, or based on detecting a loss of velocity signal which exceeds a pre-determined time period.

It is also possible to detect movement based on detecting a change in a position of a centroid of the vessel in acquired ultrasound image data, e.g. if the acquired data is color Doppler or power Doppler image data. For example, an ellipse may be fitted to the vessel as represented in the color or power Doppler data, and movement of the ellipse tracked over time, e.g. over multiple iterations of phase (b). Movement of the patient may be detected based on detecting a movement of the vessel of more than a threshold amount.

As discussed above, gate repositioning can also be triggered responsive to detecting changes in one or more hemodynamic parameters. In some examples, a combined quality metric may be defined which is based both on an amount of movement of the patient and a change in the one or more hemodynamic parameters. Re-adjustment of the Doppler gate may be triggered responsive to this combined metric falling below a threshold. By combining both of these factors, the number of re-adjustment events can be minimized, which maximizes the monitoring time.

Examples in accordance with a further aspect of the invention provide a computer program product comprising code means configured, when run on a processor, to cause the processor to perform a method in accordance with any example or embodiment outlined above or described below, or in accordance with any claim of this application.

Examples in accordance with a further aspect of the invention provide a processing arrangement adapted to perform a method in accordance with any in accordance with any example or embodiment outlined above or described below, or in accordance with any claim of this application. The processing arrangement may comprise an input/output for receiving the ultrasound data in each of phases (a) and (b) and may further comprise one or more processors adapted to perform the method in accordance with any of the example or embodiments outlined above, or in accordance with any claim of this application.

The processing arrangement may in general comprise a single processor or a plurality of processors. It may be located in a single containing device, structure or unit, or it may be distributed between a plurality of different devices, structures or units. Reference therefore to the processing arrangement being adapted or configured to perform a particular step or task may correspond to that step or task being performed by any one or more of a plurality of processing components, either alone or in combination. The skilled person will understand how such a distributed processing arrangement can be implemented. The processing arrangement includes a communication module or input/output for receiving data and outputting data to further components.

The one or more processors of the processing arrangement can be implemented in numerous ways, with software and/or hardware, to perform the various functions required. A processor typically employs one or more microprocessors that may be programmed using software (e.g., microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

A single processor or other unit may fulfill the functions of several items recited in the claims.

The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to".

Any reference signs in the claims should not be construed as limiting the scope.

The invention claimed is:

1. A method for deriving a measure of blood velocity in a blood vessel of a subject, the method performed in a single measurement session, the method comprising:
(a) in a first cardiac cycle:
acquiring ultrasound data of the blood vessel, and
determining a blood velocity profile across a radial cross-section of the blood vessel during the first cardiac cycle using the ultrasound data, based on acquiring a plurality of blood velocity measurements at different radial positions across the radial cross-section; and
(b) in one or more subsequent cardiac cycles:
acquiring ultrasound data of the blood vessel,
measuring a blood velocity at a single point within the radial cross-section of the blood vessel using the ultrasound data, and
calculating an average blood velocity across the radial cross-section of the blood vessel based on the measured blood velocity at the single point and the blood velocity profile.

2. The method as claimed in claim 1, wherein the single point is a point of maximum blood velocity.

3. The method as claimed in claim 1, wherein the determining the blood velocity profile further comprises acquiring blood velocity measurements at different circumferential positions for each of the different radial positions.

4. The method as claimed in claim 1, wherein (a) is executed once, and (b) is repeated recurrently for multiple cardiac cycles following execution of (a), using the same blood velocity profile obtained in (a).

5. The method as claimed in claim 1, further comprising obtaining an indication of at least one hemodynamic parameter of the subject and triggering re-execution of (a) responsive to detection of the at least one hemodynamic parameter meeting one or more pre-defined criteria.

6. The method as claimed in claim 5, wherein the one or more pre-defined criteria comprises a threshold value for the at least one hemodynamic parameter.

7. The method as claimed in claim 6, wherein the at least one hemodynamic parameter is obtained based on processing of the ultrasound data of the blood vessel acquired in (b).

8. The method as claimed in claim 1, wherein, in (b), the measuring the blood velocity at the single point of the blood vessel is performed using spectral Doppler ultrasound data.

9. The method as claimed in claim 1, wherein, in (a), the blood velocity profile is measured recurrently over a course of the first cardiac cycle, at different phase points of the first cardiac cycle, to acquire a respective blood velocity profile for each of the different phase points of the first cardiac cycle.

10. The method as claimed in claim 9, wherein (b) comprises determining a phase point of the one or more subsequent cardiac cycles at which the blood velocity at the single point was determined and the calculating of the average blood velocity is performed based on the blood velocity profile as measured in (a) at a corresponding phase point of the first cardiac cycle.

11. The method as claimed in claim 1, wherein (b) further comprises determining a blood flow through the blood vessel based on the calculated average blood velocity.

12. The method as claimed in claim 11, wherein (b) further comprises determining an area of the radial cross-section of the blood vessel using B-mode ultrasound data, and wherein the determining of the blood flow is based on the average blood velocity and the radial cross-section.

13. A non-transitory computer-readable medium that stores therein computer code for determining a measure of blood velocity in a blood vessel of a subject during a single measurement session, which when executed on at least one processor, causes the at least one processor to:
(a) in a first cardiac cycle:
receive ultrasound data of the blood vessel,
determine a blood velocity profile across a radial cross-section of the blood vessel during the first cardiac cycle using the ultrasound data, based on acquiring a plurality of blood velocity measurements at different radial positions across the radial cross-section; and
(b) in at least one subsequent cardiac cycle:
receive ultrasound data of the blood vessel,
measure a blood velocity at a single point within the radial cross-section of the blood vessel using the ultrasound data, and
calculate an average blood velocity across the radial cross-section of the blood vessel based on the measured blood velocity at the single point and the blood velocity profile.

14. A processing arrangement for use in determining a measure of blood velocity in a blood vessel of a subject during a single measurement session, the processing arrangement adapted to:
(a) in a first cardiac cycle:
receive ultrasound data of the blood vessel, and
determine a blood velocity profile across a radial cross-section of the blood vessel during the first cardiac cycle using the ultrasound data, based on acquiring a plurality of blood velocity measurements at different radial positions across the radial cross-section; and
(b) in one or more subsequent cardiac cycles:
receive ultrasound data of the blood vessel,
measure a blood velocity at a single point within the radial cross-section of the blood vessel using the ultrasound data, and
calculate an average blood velocity across the radial cross-section of the blood vessel based on the measured blood velocity at the single point and the blood velocity profile.

15. The processing arrangement as claimed in claim 14, further adapted to obtain an indication of at least one hemodynamic parameter of the subject and trigger re-execution of (a) responsive to detection of the at least one hemodynamic parameter meeting one or more pre-defined criteria.

16. The processing arrangement as claimed in claim 14, wherein the single point is a point of maximum blood velocity.

17. The processing arrangement as claimed in claim 14, wherein the determining the blood velocity profile further comprises acquiring blood velocity measurements at different circumferential positions for each of the different radial positions.

18. The processing arrangement as claimed in claim 14, wherein in the one or more subsequent cardiac cycles, the processing arrangement is further adapted to determine a blood flow through the blood vessel based on the calculated average blood velocity.

19. The non-transitory computer-readable medium as claimed in claim 13, wherein in the one or more subsequent cardiac cycles, the computer code further causes the at least one processor to determine a blood flow through the blood vessel based on the calculated average blood velocity.

20. The non-transitory computer-readable medium as claimed in claim 13, wherein in the one or more subsequent cardiac cycles, the computer code further causes the at least one processor to measure the blood velocity at the single point of the blood vessel using spectral Doppler ultrasound data.

* * * * *